April 6, 1976 J. H. WEINBERGER Plant Pat. 3,858
ALMOND TREE
Filed March 21, 1975
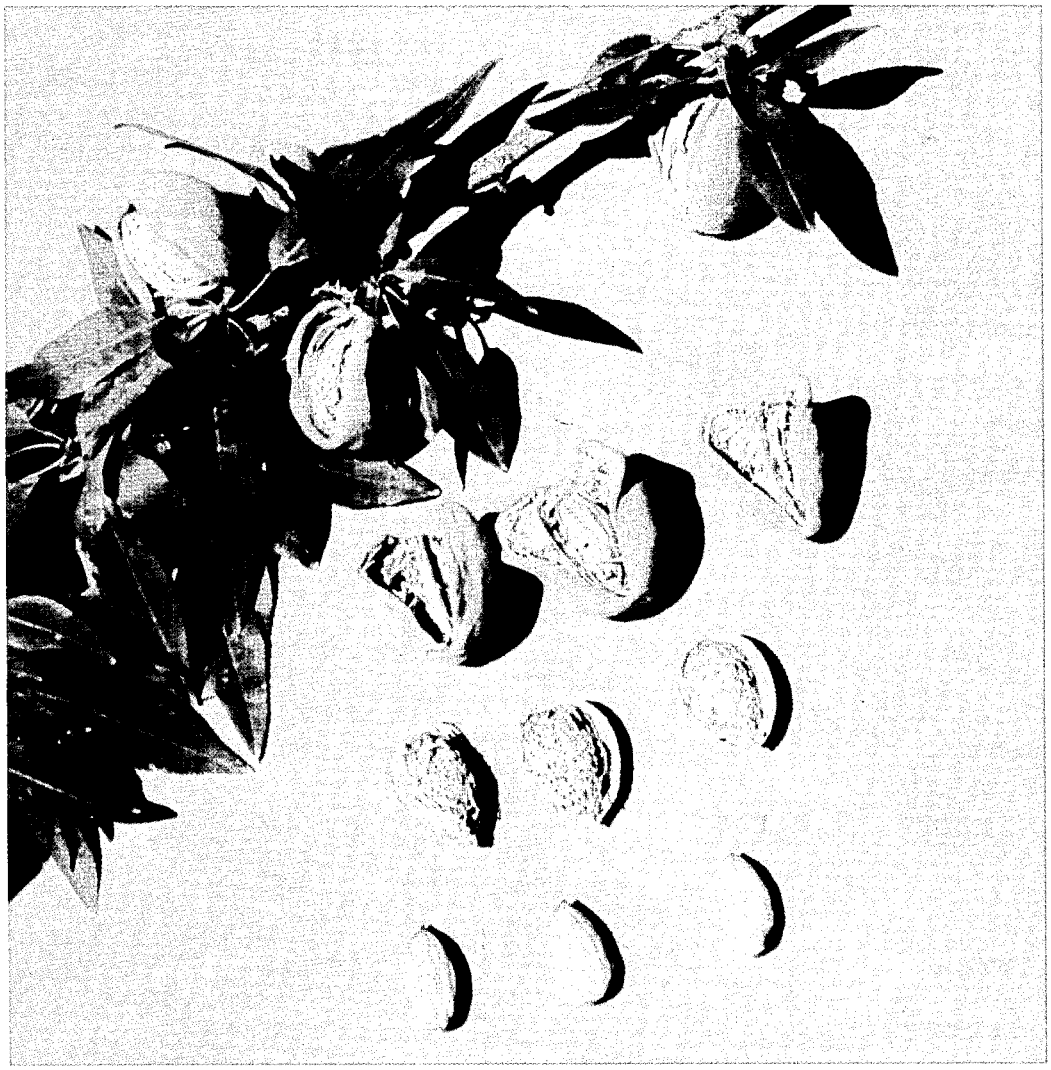

United States Patent

Plant Pat. 3,858
Patented Apr. 6, 1976

3,858
ALMOND TREE

John H. Weinberger, Fresno, Calif., assignor to
Phillip N. Jeffries, Shafter, Calif.

Filed Mar. 21, 1975, Ser. No. 560,992
Int. Cl. A01h *5/00*
U.S. Cl. Plt.—30 1 Claim

ABSTRACT OF THE DISCLOSURE

An almond tree generally characterized by medium size, medium vigor, open growth, stocky trunk and branches, a spreading branching habit, medium size, ovate, acutely pointed leaves in medium abundance, a medium blooming period, very light pink bloom in very heavy amount, and regular and very heavy bearing of early harvesting, medium size nuts having medium size kernels.

ORIGIN OF THE VARIETY

The present variety of almond tree was discovered by me growing as a mutation scaffold branch on a Nonpareil almond tree (unpatented) in an almond orchard located near Shafter, Kern County, Calif. My discovery of such mutation was occasioned by the observation—as I walked through such orchard—that one tree had a scaffold branch which bore an unusually heavy set of nuts, and which I recognized as a characteristic distinct from the remainder of the tree.

ASEXUAL REPRODUCTION OF THE VARIETY

Subsequent to my discovery of the present variety of almond tree, the variety was asexually reproduced—on my behalf—by budding on "Nemaguard" rootstock by a commercial nursery, and the trees were then planted in a growing plot near the aforesaid orchard. In maturity, such asexual reproductions ran true to the mutation scaffold branch in all respects.

SUMMARY OF THE VARIETY

The present variety of almond tree is generally characterized by medium size, medium vigor, open growth, stocky trunk and branches, a spreading branching habit, medium size, ovate, acutely pointed leaves in medium abundance, a medium blooming period, very light pink bloom in very heavy amount, and regular and very heavy bearing of early harvesting, medium size nuts having medium size kernels.

The present variety of almond tree—while most nearly resembling the Nonpareil in tree, foliage, and nuts—is more particularly and distinctively characterized, in comparison, by blooming three to five days later, by bloom more readily pollinated and fertilized, by setting fruit much more readily and which results in heavier production of nuts under similar conditions, and by production of nuts that are smaller both as to shell and kernel, the nuts having a broadly rounded base except for a small point, being smoothly ovate in edge view, and nearly oval in cross section.

BRIEF DESCRIPTION OF THE DRAWING

The drawing is an illustration, by photographic reproduction in color, of a twig with leaves and nuts as of the time of harvest; and, separately shown, nuts in hull, nuts out of hull, and kernels out of shell.

DESCRIPTION OF THE VARIETY

The botanical details of this new and distinct variety of almond tree—with color definitions in common color terms—are as follows:

Tree:
- *Density.*—Open.
- *Size.*—Medium.
- *Vigor.*—Medium.

Trunk:
- *Form.*—Stocky.
- *Texture.*—Medium, with rather shallow cracks.

Branches:
- *Form.*—Stocky.
- *Texture.*—Medium.

Lenticels:
- *Number.*—Numerous to medium.
- *Size.*—Medium to small.
- *Branching habit.*—Spreading.
- *Branching angles.*—Widely acute.
- *Color.*—New wood: Light green. Glossy. Later overlaid with thin gray epidermis. Mature wood: Grayish red or dark reddish brown.

Foliage:
- *Quantity.*—Medium.

Leaves:
- *Size.*—Medium. Average length—$3\frac{1}{32}''$. Average width—$\frac{30}{32}''$.
- *Shape.*—Ovate. Acutely pointed.
- *Thickness.*—Medium.
- *Texture.*—Smooth.
- *Margin.*—Crenate. Finely serrate.
- *Petiole.*—Long. Thick. Rigid.
- *Glands.*—Average number—2 or 3, sometimes 4. Small. Green.
- *Color.*—Top side—Medium green. Under side—Light green—dull.

Bloom:
- *Amount of bloom.*—Very heavy.
- *Color.*—Very light pink.
- *Blooming period.*—February 17th–27th. 3 to 5 days later than Nonpareil. Medium, as compared to other varieties.

Crop:
- *Bearing.*—Regular bearer.
- *Productivity.*—Very heavy.
- *Distribution of nuts on tree.*—In clusters on short spurs, and individually on terminals.
- *Ripening period.*—August 15th–20th. About with Nonpareil. Early, as compared to other varieties.
- *Tenacity.*—Hangs well on tree. Easty to harvest. Easy to hull.

Hull:
- *Outer surface.*—Smooth.
- *Pits.*—None.
- *Form.*—Regular.
- *Thickness.*—Thin.
- *Flesh.*—Tough.
- *Suture.*—Flat depressed.
- *Color.*—Light green with silvery sheen.
- *Dehiscence.*—Opens freely.
- *Splitting.*—Along ventral suture.

Nut:
- *Size.*—Medium. Average length—$1\frac{18}{64}''$. Average width—$\frac{51}{64}''$. Average thickness—$\frac{32}{64}''$. Average weight—.060 oz.
- *Form.*—Length/width: Ovate. Width/thickness: Flat.
- *Shell.*—Paper. Soft. Thin. Ragged. Outer shell: Crumbling. Adheres to hull. Inner shell: Soft. Often poorly sealed.
- *Color.*—Light to medium light brown.
- *Pits.*—Small. Numerous. Shallow. Round.
- *Base.*—Ventrally oblique.
- *Stem scar.*—Small. Obtuse.
- *Apex.*—Acuminate. Broadly curved on ventral side.
- *Wing.*—Broad. Thin. Tapered toward base.

*Inner surface.*—Light.

*Ventral streak.*—Dark. Narrow. Long. Point acute.

*Percentage of kernel to nut.*—65%.

Kernel:

*Size.*—Medium. Average length—$^{61}/_{64}$". Average width—$^{33}/_{64}$". Average thickness—$^{19}/_{64}$". Average weight—.039 oz.

*Form.*—Length/width: Ovate, with apex pointed. Dorsal and ventral edges smoothly curved. Width/thickness: Oval, rarely flat.

*Base.*—Ventrally oblique. Dorsally shouldered occasionally, but mostly rounded.

*Stem scar.*—Small. Obtuse. Dark brown.

*Apex.*—Acute. Sharp. Blunt. Prolonged at tip.

*Plumpness.*—Smooth. Slightly furrowed.

*Pellicle.*—Thin, often with small fold on ventral side. Veining distinct but not prominent.

*Pubescence.*—Short. Very smooth.

*Color.*—Medium light brown.

*Number of doubles.*—Usually none to less than 1%.

*Defective kernels.*—Gummy kernels—rare. Corky growth—rare. Blanks—about 1%. Deformed kernels—rare.

*Flavor.*—Sweet. Normal, without bitterness.

*Quality.*—Very good.

COMPARATIVE CHARACTERISTICS OF NUTS AND KERNELS

The nut of the present variety averages almost one-quarter inch less in length and almost one-eight inch less in width than the average Nonpareil nut, and the kernel of the present variety averages about one-eight inch less in length and one-sixteenth inch less in width than the average Nonpareil kernel; these distinctions causing the nut and kernel of the present variety to appear thicker or more plump than those of the average Nonpareil.

The base of the kernel of the present variety is broadly rounded and only occasionally has a shoulder on the dorsal side, whereas the kernel of the average Nonpareil has a more blunt base often with a dorsal shoulder which extends beyond the basal scar.

In edge view, the kernel of the present variety is usually smoothly ovate, with the exception of a small point, whereas—in like view—the kernel of the average Nonpareil is more often oblong-ovate with the dosal side frequently a straight line for a part of its length.

In width/thickness cross section, the kernel of the present variety is nearly oval, whereas the corresponding cross section of the kernel of the average Nonpareil is usually flattened in the thickness axis giving it an oblong-oval shape.

In addition to the nut being smaller in size, the foregoing comparative characteristics between the kernel of the present variety and that of the average Nonpareil evidence the clear distinctions which exist.

SUSCEPTIBILITY OR RESISTANCE TO INSETCS AND DISEASES

Normal susceptibility to mites. No indication of unusual shot-hole fungus or brown rot susceptibility.

The almond tree and its nut herein described may vary in slight detail due to climatic and soil conditions under which the variety may be grown; the present description being of the variety as grown in the Central Valley of California.

I claim:

1. A new and distinct variety of almond tree, substantially as illustrated and described, generally characterized by medium size, medium vigor, open growth, stocky trunk and branches, a spreading branching habit, medium size, ovate, acutely pointed leaves in medium abundance, a medium blooming period, very light pink bloom in very heavy amount, and regular and very heavy bearing of early harvesting, medium size nuts having medium size kernels; the variety—while most nearly resembling the Nonpareil in tree, foliage, and nuts—being distinctively characterized, in comparison, by blooming three to five days later, by bloom more readily pollinated and fertilized, by setting fruit much more readily and which results in heavier production of nuts under similar conditions, and by production of nuts that are smaller both as to shell and kernel, the nuts having a broadly rounded base except for a small point, being smothly ovate in edge view, and nearly oval in cross section.

No references cited.

ROBERT E. BAGWELL, Examiner